(12) United States Patent
Almeida et al.

(10) Patent No.: US 10,464,913 B2
(45) Date of Patent: *Nov. 5, 2019

(54) PROCESS FOR THE PREPARATION OF A PURIFIED ACID COMPOSITION

(71) Applicant: Synvina C.V., Amsterdam (NL)

(72) Inventors: Ana Rita Martins Guerreiro Rocha Almeida, Amsterdam (NL); Martinus Mathilda Pieter Zieverink, Amsterdam (NL); Ana Sofia Vagueiro De Sousa Dias, Amsterdam (NL); Ines Dacil Gonzalez Jimenez, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/579,256

(22) PCT Filed: Jun. 6, 2016

(86) PCT No.: PCT/NL2016/050405
§ 371 (c)(1),
(2) Date: Dec. 4, 2017

(87) PCT Pub. No.: WO2016/195500
PCT Pub. Date: Dec. 8, 2016

(65) Prior Publication Data
US 2018/0155308 A1    Jun. 7, 2018

(30) Foreign Application Priority Data

Jun. 5, 2015 (NL) .................................... 2014923

(51) Int. Cl.
| | | |
|---|---|---|
| *C07D 307/68* | (2006.01) | |
| *B01J 23/34* | (2006.01) | |
| *B01J 23/75* | (2006.01) | |
| *B01J 27/08* | (2006.01) | |
| *C07B 31/00* | (2006.01) | |
| *C07B 33/00* | (2006.01) | |
| *C07B 41/02* | (2006.01) | |
| *C07B 63/02* | (2006.01) | |

(52) U.S. Cl.
CPC ............ *C07D 307/68* (2013.01); *B01J 23/34* (2013.01); *B01J 23/75* (2013.01); *B01J 27/08* (2013.01); *C07B 31/00* (2013.01); *C07B 33/00* (2013.01); *C07B 41/02* (2013.01); *C07B 63/02* (2013.01); *B01J 2219/00033* (2013.01); *B01J 2219/00051* (2013.01); *B01J 2219/00162* (2013.01)

(58) Field of Classification Search
CPC .................................................. C07D 307/68
USPC ....................................................... 549/485
See application file for complete search history.

(56) References Cited

U.S. PATENT DOCUMENTS

| | | | |
|---|---|---|---|
| 5,420,344 A | 5/1995 | Izumisawa et al. | |
| 6,441,241 B1 | 8/2002 | Cortright et al. | |
| 8,519,167 B2 | 8/2013 | Munoz De Diego et al. | |
| 8,969,404 B2 * | 3/2015 | Janka .................. | C07D 307/68 514/438 |
| 2012/0302773 A1 * | 11/2012 | Janka .................. | C07D 307/68 549/485 |
| 2014/0128623 A1 * | 5/2014 | Janka .................. | C07D 307/68 549/485 |
| 2014/0142328 A1 | 5/2014 | Shaikh et al. | |

FOREIGN PATENT DOCUMENTS

| | | | |
|---|---|---|---|
| EP | 2486027 B1 | 6/2014 | |
| EP | 2784069 B1 | 7/2016 | |
| JP | H5-190908 A | 7/1993 | |
| JP | H9-151162 A | 6/1997 | |
| JP | 2002-519336 A | 7/2002 | |
| JP | 2008-524198 A | 7/2008 | |
| WO | 00/00457 A1 | 1/2000 | |
| WO | 2006/085134 A1 | 8/2006 | |
| WO | 2011/043661 A1 | 4/2011 | |
| WO | 2013/191943 A1 | 12/2013 | |
| WO | 2013/191944 A1 | 12/2013 | |
| WO | WO 2013191943 | * 12/2013 | ........... C07D 307/68 |
| WO | WO 2013191944 | * 12/2013 | ........... C07D 307/68 |
| WO | 2014/163500 A1 | 10/2014 | |
| WO | 2015/030590 A1 | 3/2015 | |

OTHER PUBLICATIONS

Japanese Office Action for Japanese Application No. 2017-563100, dated Nov. 26, 2018.

\* cited by examiner

Primary Examiner — Nizal S Chandrakumar
(74) Attorney, Agent, or Firm — Hoffmann & Baron, LLP

(57) ABSTRACT

A purified acid composition including 2,5-furandicarboxylic acid is prepared in a process, including oxidizing a feedstock containing 5-alkoxymethylfurfural to an oxidation product including 2,5-furandicarboxylic acid (FDCA) and 2-formyl-furan-5-carboxylic acid (FFCA), and esters of FDCA and, optionally, esters of FFCA; hydrolyzing the at least part of the oxidation product in the presence of water, thereby hydrolyzing at least esters of FDCA and, optionally, esters of FFCA to obtain an aqueous solution of an acid composition including FDCA, FFCA and ester of FDCA in an amount below the amount of ester of FDCA in the solution of the oxidation product; contacting at least part of the solution of the acid composition with hydrogen in the presence of a hydrogenation catalyst to hydrogenate FFCA to hydrogenation products, yielding a hydrogenated solution; and separating at least a portion of the FDCA from at least part of the hydrogenated solution by crystallization.

19 Claims, 3 Drawing Sheets

PROCESS FOR THE PREPARATION OF A PURIFIED ACID COMPOSITION

CROSS-REFERENCE TO RELATED APPLICATIONS

This application is the National Stage of International Application No. PCT/NL2016/050405 filed Jun. 6, 2016, which claims the benefit of Netherlands Application No. NL 2014923, filed Jun. 5, 2015, the contents of which is incorporated by reference herein.

FIELD OF THE INVENTION

The present invention relates to a process for the preparation of a purified acid composition. In particular it relates to the preparation of a purified composition that comprises 2,5-furandicarboxylic acid.

BACKGROUND OF THE INVENTION 2,5-Furandicarboxylic acid (FDCA) is a chemical in which interest has been growing recently. It is for instance seen as an alternative for terephthalic acid in the manufacture of polyesters. The advantage of FDCA resides in that it can be obtained from renewable resources, whereas terephthalic acid is obtained from p-xylene that is recovered from fossil fuels. FDCA can be synthesized by the oxidation of 5-hydroxymethylfurfural (HMF) and/or ethers and/or esters thereof. The oxidation reaction has inter alia been described in WO 2011/043661 and U.S. Pat. No. 8,519,167.

In such oxidation reactions not only FDCA is produced, but also some by-products, including colorants, also known as color bodies. Another one of such by-products is 5-formyl-2-furan carboxylic acid (FFCA). This by-product is a mono-carboxylic acid. Its presence in an FDCA composition is undesirable, since the mono-carboxylic acid will terminate the chain growth during polymerization. It has been found that it is difficult to remove FFCA by crystallization from an acid composition comprising FDCA and FFCA. This problem has been acknowledged in the art. In U.S. Pat. No. 8,969,404 a purification method is described wherein a crude composition that contains FDCA, is subjected to selective hydrogenation in order to convert by-products, such as color bodies and FFCA, to more innocuous products that can be more easily separated from FDCA. This purification method is analogous to the purification of crude terephthalic acid that contains 4-carbonyl-benzoic acid as by-product. In the case of terephthalic acid 4-carbonyl-benzoic acid is selectively hydrogenated to p-toluic acid, which can be easily separated from terephthalic acid.

U.S. Pat. No. 8,969,404 teaches that the hydrogenation of FFCA may result in 5-hydroxymethyl-2-furancarboxylic acid (HMFA), 5-methyl-2-furancarboxylic acid (MFA), 2-hydroxymethylfuran and furan-2-carboxylic acid (FCA). In addition, the hydrogenation may also lead to the saturation of the furan ring in FDCA, leading to 2,5-tetrahydrofuran-dicarboxylic acid (THFDCA). According to U.S. Pat. No. 8,969,404 all these hydrogenation products can be easily separated from FDCA through any number of techniques, such as crystallization. The hydrogenation can be carried out at a very broad range of conditions, viz. at a hydrogen partial pressure of 10 to 900 psi (0.69 to 62.05 bar), at a temperature of 130 to 225° C. for a period in the range of 15 min to 10 hrs. In experiments hydrogenation reactions are conducted at a hydrogen partial pressure of 75 to 231 psi (5.17 to 15.93 bar) and a temperature of 150 to 200° C. for 1 or 3 hrs. When higher pressures were used the results deteriorated significantly since excessive ring hydrogenation occurred to form THFDCA.

By means of these experimental data U.S. Pat. No. 8,969,404 suggests that the amount of THFDCA can be controlled at high hydrogen partial pressure or high hydrogenation temperatures by limiting the amount of hydrogenation catalyst and by limiting the residence time. Although U.S. Pat. No. 8,969,404 shows the amounts of FFCA and THFDCA in hydrogenated FDCA compositions, it fails to show what the levels of other by-products are in the hydrogenated and purified FDCA composition. Neither does it mention what the loss of FDCA is at the reaction conditions applied. It does mention though that severe hydrogenation conditions, i.e. at high temperature and in the presence of palladium catalyst, decarboxylation or hydrogenolysis of FDCA or THFDCA may occur. It is evident that such decarboxylation reaction leads to further losses of the desired FDCA product. U.S. Pat. No. 8,748,479 teaches a similar process.

US2014/128623 claims the preparation of esters of purified FDCA as plasticizer. It describes a possible method of producing purified FDCA by hydrogenation of contaminated FDCA and separating a hydrogenation species from the hydrogenation product. No indication has been given what species is separated nor how the species is separated. The specification teaches that the hydrogenation reaction takes four hours.

US 2014/142328 discloses a process to produce a dry purified carboxylic acid product comprising furan-2,5-dicarboxylic acid (FDCA) by oxidizing a feed stream comprising at least one oxidizable compound to generate a crude carboxylic acid slurry comprising FDCA. Impurities are removed therefore via oxidative purification in a post-oxidation zone. In addition, FDCA may further be decolorized via hydrogenation. No further details on the hydrogenation have been provided.

As indicated in U.S. Pat. No. 8,969,404 the crude acid composition comprising FDCA may be obtained from the catalytic oxidation of 5-hydroxymethyl furfural (HMF) or esters or ethers thereof or mixtures of HMF and an ester or ether thereof. It is known that the oxidation of ethers of HMF results in a mixture of FDCA and an ester thereof. Such is shown in e.g. U.S. Pat. No. 8,519,167. According to U.S. Pat. No. 8,969,404 the oxidation product which is a crude FDCA composition which will then also comprise an amount of FDCA ester, is combined with a hydrogenation solvent to obtain solvated FDCA and FFCA. Solvated FDCA also contains esters of FDCA. The solvated combination is then subjected to hydrogenation, which according to U.S. Pat. No. 8,969,404 may take 1 to 3 hours. It is undesirable to subject the solvated FDCA composition to catalytic hydrogenation since it has been generally described that the catalytic conversion of carboxylic acids to alcohols is more difficult than the conversion of esters to alcohols. Such is confirmed in U.S. Pat. No. 6,441,241. Hence, if the solvated FDCA composition, comprising FDCA, FFCA and esters of FDCA and, optionally, of FFCA, is subjected to catalytic hydrogenation, as taught in U.S. Pat. No. 8,969,404, there is a possibility that the esters that are present in the solvated FDCA composition will be converted to the alcohols, which leads to a yield loss. Therefore, the present inventors have found that such solvated FDCA compositions are to be subjected to a hydrolysis step before the resulting converted composition is subjected to hydrogenation.

Further, in confirmation of the teachings of U.S. Pat. No. 8,969,404, it has been found that some FCA is formed during the hydrogenation of an FDCA-containing composition. FCA, being a monocarboxylic acid, is as undesired as FFCA. It has now appeared that the purification of the hydrogenated product is detrimentally affected by the presence of an ester of FDCA. The more ester is present in the hydrogenated product, the more FCA is retained therein. It is therefore important to reduce the levels of ester of FDCA in the oxidation product before such oxidation product is subjected to hydrogenation in order to facilitate the separation of FDCA in the hydrogenated product in the desired purity.

SUMMARY OF THE INVENTION

Accordingly, the present invention provides a process for the preparation of a purified acid composition comprising 2,5-furandicarboxylic acid, comprising
(i) oxidizing a feedstock containing 5-alkoxymethylfurfural to an oxidation product comprising 2,5-furandicarboxylic acid (FDCA) and 2-formyl-furan-5-carboxylic acid (FFCA), and esters of FDCA and, optionally, esters of FFCA;
(ii) optionally, dissolving at least part of the oxidation product in a polar solvent to obtain a solution of the oxidation product, comprising FDCA, FFCA and esters of FDCA and, optionally, esters of FFCA;
(iii) hydrolyzing the at least part of the oxidation product in the presence of water, thereby hydrolyzing at least esters of FDCA and, optionally, esters of FFCA to obtain an aqueous solution of an acid composition comprising FDCA, FFCA and ester of FDCA in an amount below the amount of ester of FDCA in the solution of the oxidation product;
(iv) contacting at least part of the solution of the acid composition obtained in step (iii) with hydrogen in the presence of a hydrogenation catalyst to hydrogenate FFCA to hydrogenation products, yielding a hydrogenated solution; and
(v) separating at least a portion of the FDCA from at least part of the hydrogenated solution by crystallization. The FDCA or the portion thereof that is separated in step (v) is the desired purified FDCA-containing acid composition.

The hydrolysis reaction is an equilibrium reaction. The present inventors surprisingly have found that when the crude acid composition also contains an ester of FDCA, the hydrogenation of the crude acid composition over a hydrogenation catalyst appears to enhance the conversion of the ester. Hence, the process according to the present invention is very suitable for the situation when the crude acid composition has been obtained by the hydrolysis of the oxidation product of a 5-alkoxymethyl furfural. In order to obtain a purified FDCA composition, the oxidation product is hydrolyzed to convert the alkyl ester to FDCA itself. Due to the finding that the presence of a hydrogenation catalyst also appears to benefit the conversion of the ester of FDCA, the hydrolysis reaction can be accomplished without any specific measure. The effluent of the hydrolysis reaction may thus still contain some ester of FDCA.

The oxidation of the feedstock containing 5-alkoxymethylfurfural is known in the art. In this context reference is made to EP 2486027. In accordance with the teachings of this patent specification the feedstock in step (i) is suitably oxidized by means of an oxygen-containing gas in the presence of a catalyst that comprises cobalt and manganese. The oxygen-containing gas may be selected from air, oxygen-enriched air, oxygen-depleted air or pure oxygen. Optionally, other inert gases, such as nitrogen, helium, neon or argon, may be added to any of these oxygen-containing gases. Preferably, the catalyst further comprises bromine, in addition to cobalt and manganese. The feedstock is suitably oxidized at a temperature of 60 to 220° C., at a pressure of from 5 to 100 bar and a residence time of from 0.1 to 48 hours. The oxidation is suitably carried out in the presence of a solvent. Suitable solvents include carboxylic acids, typically with 1 to 4 carbon atoms. More preferably, the solvent is acetic acid and/or acetic anhydride. The alkyl group in 5-alkoxymethyl furfural is suitably an alkyl group containing 1 to 4 carbon atoms, and is preferably methyl. The feedstock containing 5-alkoxymethylfurfural contains thus with particular preference 5-methoxymethylfurfural (MMF). The feedstock does not need to consist solely of the alkoxymethylfurfural. The feedstock may comprise other components, suitably in an amount of up to 20% wt. A suitable component that may be contained in the feedstock is 5-hydroxymethylfurfural (HMF), which thus may be present in the feedstock in an amount of up to 20% wt. The oxidation product thus obtained is optionally recovered as product and subjected to one or more treatments. Such treatments include the recovery of the oxidation product by separating the oxidation product from any of the other components that may have been present in the oxidation. Such components may be the catalyst and the solvent. Suitable separation treatments include wash treatments and/or crystallization. After such treatments the oxidation product mainly consists of FDCA, FFCA and esters of FDCA and FFCA.

When the oxidation takes place in a carboxylic acid as solvent it is suitable to replace the acid by a polar, preferably aqueous, solvent in order to subject the oxidation product to hydrolysis, thereby creating an oxidation product solution. Very suitably the polar solvent is therefore water.

In step (iii) at least a part of the oxidation product is subjected to hydrolysis. Suitably, the entire oxidation product is hydrolyzed, albeit that it may have been crystallized and washed in order to remove catalyst and solvent remainders before hydrolysis. The at least part of the oxidation product is suitably hydrolyzed by contacting the at least part of the oxidation product with water in the presence of a hydrolysis catalyst. The catalyst can be selected from a wide range of acid or alkaline compounds. It is most convenient to apply inorganic acids, such as sulfuric acid, hydrochloric acid, nitric acid, phosphoric acid and the like. Also the use of Lewis acids, such as aluminum trichloride, may be used. The use of combinations of acids, both Brønsted acids and Lewis acids, is feasible. Suitable alkaline catalysts include the alkali metal hydroxides, such as sodium or potassium hydroxide, but salts of weak organic acids may also be used. Salts of formic acid, acetic acid, propionic acid or butyric acid are suitable examples. The cation can be any metal ion, such as an alkali metal ion or alkaline earth metal ion. Other metal salts of such weak organic acids, such as the zinc salts, may also be used. It is advantageous if the salts are soluble in water. The skilled person will realize that the nature of the hydrolysis catalyst is not of critical importance. Further, also heterogeneous acid catalysts, such as acidic ion exchange resins and acidic zeolites, may be used. Examples of acidic ion exchange resins are styrene-divinyl benzene resins that contain acid groups, such as sulfonic acid groups. Commercial resins are sold under the trade mark Amberlyst (by Rohm and Haas). Acidic zeolites may include zeolites X, zeolite Y, mordenite, zeolite beta, ZSM-5, ZSM-11 and other zeolites, which are at least partly converted to their protonated form.

Since the oxidation product already comprises a significant amount of acid in the form of FDCA and FFCA, there may be no need to add additional acid catalyst. Accordingly, the at least part of the oxidation product is preferably hydrolyzed by contacting the at least part of the oxidation product with water in the absence of a hydrolysis catalyst.

The amount of ester of FDCA in the oxidation product may vary within broad ranges. When the feedstock to be oxidized comprises only 5-alkoxymethyl furfural, the proportion of the ester of FDCA can be very high. Dependent on the alkyl group of the 5-alkoxymethyl furfural the proportion can be very high, e.g. up to 90% wt, based on the amounts of FDCA and the ester thereof. In EP2784069 examples for the oxidation of 5-butoxymethyl furfural are described wherein the predominant product is the monobutyl ester of FDCA. However, WO 2014/163500 discloses examples for a process for the oxidation of 5-methoxymethyl furfural, wherein more than 85% wt of FDCA is obtained and less than 15% wt of the monomethyl ester of FDCA. The amount of the ester of FDCA in the oxidation product can therefore be as high as more than 90% wt. For the process according to the invention the amount of ester of FDCA in the at least part of the oxidation product that is hydrolyzed, suitably comprises from 0.5 to 90% wt, preferably from 0.5 to 60% wt of ester of FDCA, based on the amounts of FDCA, FFCA and esters of FDCA and FFCA.

In the hydrolysis the proportion of the ester is reduced. Any reduction has already advantages over the original proportion. It is especially advantageous when an amount of ester of FDCA in the aqueous solution of an acid composition is at most 5.0% wt, preferably at most 1.0% wt, based on the amount of FDCA, FFCA, and esters of FDCA and FFCA. In such a case the hydrogenation conditions may be sufficient to reduce the eventual level of the ester of FDCA in the purified FDCA that is obtained after crystallization to a level that is innocuous, such as e.g. up to 5000 ppm or less, more preferably up to a level of 2500 ppm or less, most preferably to a level of 1000 ppm or less.

Hydrolysis conditions are well known in the art. It is conventional to heat the ester in water in the presence or absence of an acid or a base. A suitable temperature range may be from 100 to 220° C. Since in the present case it has been found that it is advantageous to conduct the hydrolysis at temperatures above 100° C., it is desirable to apply a pressure above 1 bar. Therefore, the at least part of the oxidation product is preferably contacted with water at a temperature of 120 to 200° C. and a pressure of 5 to 80 bar, preferably from 5 to 40 bar in step (iii).

The conditions of the hydrolysis can be selected such that the equilibrium is virtually reached. That may take some residence time. However, when the amount of ester of FDCA is relatively low, there is no need to reach the equilibrium, and the contact time may then also be relatively short. Therefore, in step (ii) the at least part of the oxidation product is suitably hydrolyzed by contacting the at least part of the oxidation product with water for a period from 1 to 360 minutes, preferably from 1 to 300 minutes, more preferably from 1 to 5 hours.

As indicated above the level of ester of FDCA may vary between wide ranges. The level of ester of FDCA can be relatively high. On the other hand it is also advantageous to perform the hydrolysis on a composition that comprises a limited amount of ester since the hydrogenation appears to facilitate the conversion of the ester of FDCA. The eventual hydrolysis may then even result in a level of ester below the hydrolysis equilibrium. Therefore, it is feasible to perform a number of hydrolysis steps on the oxidation product wherein after each step some FDCA or alcohol is removed to shift the equilibrium for the subsequent step. The level of the ester of FDCA in the last hydrolysis step is then sufficiently reduced to satisfactorily benefit from the effect of the hydrogenation treatment on the hydrolysis. Such sequence comprises a number of hydrolysis reactors and FDCA removal treatments. It has been found that preferably the part of the oxidation product that is hydrolyzed has been obtained by:

separating the oxidation product into at least an oxidation product solids fraction comprising FDCA, and an oxidation product liquid fraction comprising ester of FDCA;

pre-hydrolyzing at least a portion of the oxidation product liquid fraction by contacting the at least portion of the oxidation product liquid fraction with water to obtain a pre-hydrolyzed composition comprising FDCA and ester of FDCA; and combining at least a portion of the oxidation product solids fraction with at least a portion of the pre-hydrolyzed composition.

In this case the oxidation product which typically becomes available in the form of a slurry in a solvent or diluent, is suitably subjected to a solids/liquid separation step, e.g. a filtration step. Such can be very advantageous since then solids may contain relatively pure FDCA containing a reduced amount of ester of FDCA compared with the amount of ester of FDCA in the oxidation product, whereas the ester of FDCA will be concentrated in the mother liquor. After separation of at least part of the solvent or diluent, such as acetic acid, at least a part of the remaining composition which is rich in ester of FDCA, is admixed with an aqueous liquid to ensure that it is contacted with water to achieve a pre-hydrolysis. The pre-hydrolysis may be carried out such that it is substantially complete, but such is not required. The pre-hydrolyzate thus obtained is partly or completely combined with at least a portion of the oxidation product solids fraction. If the pre-hydrolyzate is available in the form of an aqueous solution, the solids oxidation product fraction can be combined with the pre-hydrolyzate and be dissolved therein. Alternatively, when the pre-hydrolyzate is made available in the form of pre-hydrolyzate solids fraction this solid fraction may be combined with the solids from the oxidation product and subsequently be dissolved. In such a case the pre-hydrolyzate solids fraction is typically separated from the pre-hydrolyzed composition and at least a portion of said pre-hydrolyzate solids fraction is combined with the at least portion of oxidation product solids fraction. The combined fractions, optionally after dissolution in a polar solvent, such as water, still contain ester of FDCA, although the proportion thereof has been reduced compared with its proportion in the oxidation product. Advantageously, the level of ester of FDCA is in the range of 0.5 to 5.0% wt, preferably from 0.5 to 2.0% wt. These low levels allow for a very efficient hydrolysis in a step (iii) which hydrolysis is led to virtual completion during the hydrogenation in step (iv).

The product resulting from the hydrolysis in step (iii) is an aqueous solution of a crude acid composition. This composition comes available in the form of an aqueous solution of this composition in the solvent in which the hydrolysis has been conducted. This solvent typically contains water and may further comprise an alcohol, e.g. the alcohol that is liberated by the hydrolysis of the ester-containing oxidation product. As the feedstock comprises 5-alkoxymethylfurfural the solvent after hydrolysis will comprise the corresponding alkyl alcohol. This solution may be used as obtained. Alternatively, the hydrolyzed product may be recovered from the effluent of the hydrolysis reaction, e.g. by crystallization. If such recovery is undertaken, the crystallized hydrolyzed product may also be subjected to further treatments, such as a wash treatment and/or optionally a drying treatment.

Typically the contact of the oxidation product with water will lead to a solution of FDCA, ester of FDCA and FFCA, constituting the acid composition solution that is to be hydrogenated. If, due to any treatments, the product after hydrolysis comprising FDCA and FFCA is obtained as solid material, this product is at least partly dissolved in a polar solvent to obtain an acid composition solution to be contacted with hydrogen in accordance with step (iv) of the process according to the invention. If the oxidation product after hydrolysis is obtained as a solution comprising FDCA and FFCA, the solution may be used as the acid composition solution mentioned in step (iv) of the process according to the invention.

In step (iv) of the process at least part of the acid composition solution is contacted with hydrogen in the presence of a hydrogenation catalyst in order to hydrogenate FFCA that is present in the solution. Suitably the entire acid composition solution is subjected to the contact with hydrogen. It has now been found that in contradiction to the teachings of U.S. Pat. No. 8,969,404 it is not easy to separate some of the hydrogenation products of FFCA from FDCA. In particular, it has been found that it is rather difficult to separate MFA from a solvated mixture that contains both FDCA and MFA. None of the prior art documents have found that the presence of MFA is an important parameter in the purification of crude FDCA. The present invention is also based on the finding that the purification of a composition that contains both FDCA and FFCA is to be carried out by conducting a hydrogenation thereof in such a way that the amount of MFA produced is reduced. Suitably, FFCA is hydrogenated in step (iv) such that the hydrogenation products contain up to a minor amount of 2-methyl-furan-5-carboxylic acid (MFA). By the expression "minor amount" is understood up to 50% wt of the hydrogenation products of FFCA. Step (iv) also includes the situation wherein no MFA is present at all.

Step (iv) is suitably carried out in the way described as follows. It has been found that the skilled person can control the amount of MFA produced, by adjusting the hydrogenation conditions. In particular, it has been found that by adjusting the residence time to values that are significantly shorter than the reaction duration as taught by U.S. Pat. No. 8,969,404 the level of MFA can be controlled. That has the additional advantage that not only the separation of the desired FDCA is facilitated, but also that no ring hydrogenation of FDCA occurs, thereby benefiting the yield of desired FDCA. Moreover, the decarboxylation of FDCA to FCA as suggested in U.S. Pat. No. 8,969,404 can be kept to a satisfactorily low level by reducing the residence time. It has been found that preferably the acid composition solution is contacted with hydrogen at a temperature in the range of 150 to 200° C. and for a contact time with the hydrogenation catalyst of less than 0.25 hour. The contact time is suitably in the range of 5 seconds to 15 min, preferably from 5 seconds to 14 min, more preferably from 5 seconds to 12 min, most preferably, from 5 seconds to 10 min. Without wishing to be bound by any theory, it is believed that FFCA is first hydrogenated to 5-hydroxymethyl-2-furancarboxylic acid (HMFA), which is then further hydrogenated to MFA. HMFA and MFA obtained may be hydrogenated to other products. It has further been found that the conversion of FFCA to 5-hydroxymethyl-2-furan carboxylic acid (HMFA) proceeds very fast. In order to prevent further hydrogenation of HMFA to, for example, MFA, the contact time of FFCA with the hydrogenation catalyst is preferably at most 10 min, more preferably at most 3 min, most preferably at most 1 min. The contact time may be shorter dependent on the concentration of FDCA in the acid composition solution. For instance, when the concentration in this solution amounts to less than 40% wt, the contact time is preferably lower than 10 min. At a concentration of FDCA in the acid composition solution of 0.5 to 35% wt, the contact time is preferably from 5 sec. to 3 min, more preferably from 5 sec to 1 min. The contact time may also be shortened dependent on the hydrogenation temperature. The contact time will be very short when the reaction temperature is in the upper part of the range of 150 to 200° C. and all FDCA is dissolved, e.g. in the range of 5 sec. to 1 minute. At reaction temperatures in the lower part of the range, the contact time may amount to about one minute. The short contact time results in very little production of MFA, if any, whereas a major part of the hydrogenation product of FFCA consists of HMFA. Since HMFA is better soluble in polar solvents, such as water, than FDCA the crude acid composition can be purified by crystallizing FDCA from the hydrogenated solution whilst HMFA remains in the mother liquor. The crystallized FDCA then represents the purified acid composition. HMFA can be recovered from the mother liquor and recycled to the oxidation, thereby enabling to increase the yield of FDCA.

Alternatively, the acid composition solution is suitably contacted with hydrogen at a temperature in the range of 150 to 200° C. and for a contact time with the hydrogenation catalyst of 3 to 15 min, preferably from 3 to 10, more preferably from 3 to 8 min. By prolonging the contact time with the hydrogenation catalyst to up to a quarter of an hour, it appeared that the hydrogenation products of FFCA no longer contained any HMFA and also contained none or only a minor amount of MFA, whereas the amount of 2,3,4,5-tetrahydrofuran compounds, such as the tetrahydrofuran-2,5-dicarboxylic acid, was still virtually zero.

Thus, the acid composition solution is preferably contacted with hydrogen at a temperature in the range of 150 to 200° C. and a contact time with the hydrogenation catalyst of less than 0.25 hour. The contact time is suitably in the range of 5 seconds to 15 min, preferably from 5 seconds to 14 min. Even more preferably, the contact time of the acid composition solution with the hydrogenation catalyst is at most 10 min. Alternatively, the contact time is suitably from 3 to 15 minutes.

The hydrogenation catalyst may be selected from a wide variety of available catalysts. Typically, the hydrogenation catalyst comprises one or more metals or metal compounds selected from the metals in the Groups 8 to 10 of the Periodic Table of Elements on a carrier. Such suitable metals include Pt, Pd, Ru, Rh, Ir, Os, Ni, Co and mixtures thereof.

The carriers for these metals may be selected from a variety of conventional carriers. Preferably, the carrier has been selected from alumina, silica, titania, zirconia, silica-alumina and carbon, such as activated carbon. The skilled person will know that activated carbon is an amorphous form of carbon with a surface area of at least 600 m$^2$/g. Such activated carbon thus has a porous structure.

The hydrogenation catalyst preferably comprises palladium on carbon.

The loading of the metal or metals on the carrier may also be varied within wide ranges. The content of metal on the hydrogenation catalyst may be in the range of 0.1 to 25% wt, more suitably from 0.2 to 10% wt, preferably from 0.3 to 5% wt, based on the weight of the hydrogenation catalyst.

The amount of hydrogen in the hydrogenation reaction of FFCA is controlled by adjusting the pressure of the hydrogen-containing gas and/or the percentage of hydrogen in the gaseous atmosphere that is present in the reaction. Suitably, the total pressure at the reaction is within the range of 1 to 80 bar, preferably from 2 to 50 bar, more preferably from 5 to 40 bar. The lower limit of the pressure range may thus be 1 bar, or 2 bar or 5 bar, whereas the upper limit of the pressure range may be 80 bar, or 50 bar or 40 bar. Hydrogen may be supplied as pure hydrogen gas or as a mixture of hydrogen with an inert gas, such as nitrogen, argon, neon, xenon or mixtures thereof. The hydrogen content in the hydrogen-containing gas is suitably in the range of 1 to 100% vol, preferably from 2 to 100% vol, more preferably from 5 to 100% vol. In some embodiments the hydrogen-containing gas contains a major part of inert gases, such as nitrogen, helium, neon or argon. In this way the hydrogen partial pressure can be limited, whereas the total reaction pressure can be maintained at a sufficiently high level. The hydrogen partial pressure in the reaction can therefore suitably range from 0.1 to 80 bar, depending on the total pressure and on the proportion of hydrogen in the hydrogen-containing gas.

Especially since the contact time with the hydrogenation catalyst is relatively short, compared with the reaction times in U.S. Pat. No. 8,969,404, the present process is excellently suited for being conducted as a continuous process. That entails a significant advantage over the process exemplified in U.S. Pat. No. 8,969,404. Examples of this known process are carried out as a batch process for a period of 1 to 3 hours. When such long reaction times are to be applied, large reactors and/or slow supplies of feedstock to the reactors are to be used. In contrast therewith, the process according to the present invention may comprise a contact time as short as less than 15 minutes. With such short contact times it is preferable to conduct the process in a continuous mode. The reactor in which such a continuous process takes place may comprise a continuous stirred tank reactor, a bubble column reactor, a trickle flow reactor or a plug flow reactor. Preferably, the process is carried out in a fixed bed reactor, wherein the acid composition solution is passed, preferably downward, over a bed of hydrogenation catalyst. In such a process the acid composition solution is optionally contacted with hydrogen before it is contacted with the hydrogenation catalyst so that it is pre-saturated with hydrogen. Alternatively, hydrogen may be passed either co-currently or counter-currently along the fixed bed of hydrogenation catalyst.

The crude acid composition has been dissolved in a polar solvent. The polar solvent may suitably be selected from any liquid that is able to dissolve the crude acid composition in a satisfactory concentration. The polar solvent is therefore suitably selected from the group consisting of water, alcohols, acids and mixtures thereof. The alcohol is suitably selected from the group consisting of $C_1$-$C_4$ mono-alcohols and mixtures thereof. Examples of suitable acids that can be used as polar solvents are $C_1$-$C_6$ carboxylic acids, in particular acetic acid or acetic anhydride. In such a solvent the crude acid composition may have been obtained, e.g. by the oxidation of HMF ethers. In such oxidation water is liberated. The use of such a carboxylic acid has the advantage that no solvent swap has to be carried out to hydrogenate the crude acid composition. Most preferably, the solvent is selected from water, methanol and a mixture thereof. If desired, the polar solvent may be made substantially free from one or more alcohols. This can be done via a stripping technique. For stripping any inert gas can be used, e.g. nitrogen, carbon dioxide or steam. Also hydrogen-containing gas that is used for the hydrogenation, can be used as stripping gas. In that way the crude acid composition may be present in a single solvent, e.g. water. The concentration of the crude acid composition may be as high as 35% wt, based on the total of crude acid composition and polar solvent, and is typically at least 5% wt. Preferably, the concentration of the crude acid composition in the polar solvent is in the range of 7 to 30% wt, based on the total of crude acid composition and polar solvent.

Suitable hydrogenation conditions can thus be summarized as follows; the hydrogen partial pressure is preferably in the range of 0.1 to 80 bar, or 0.2 bar to 80 bar or 0.5 bar to 80 bar, more preferably from 0.2 to 50 bar, and most preferably from 0.5 to 40 bar. The hydrogenation catalyst may be as described above, i.e. preferably comprising one or more metals or metal compounds selected from the metals in the Groups 8 to 10 of the Periodic Table of Elements on a carrier. Such suitable metals include Pt, Pd, Ru, Rh, Ir, Os, Ni, Co and mixtures thereof. The content of metal on the hydrogenation catalyst may be in the range of 0.1 to 25% wt, more suitably from 0.2 to 10% wt, preferably 0.3 to 5% wt, based on the weight of the hydrogenation catalyst.

The carriers for these metals may be selected from a variety of conventional carriers. Preferably, the carrier has been selected from alumina, silica, titania, zirconia, silica-alumina and carbon, such as activated carbon. The skilled person will know that activated carbon is an amorphous form of carbon with a surface area of at least 600 m$^2$/g. Such activated carbon thus has a porous structure. Very high surface areas of porous charcoals made from wood and peat, as well as those derived from more exotic materials such as coconut husks, are well suited as catalyst supports. They are used widely to prepare catalysts containing noble metals, such as Pt, Pd, Ru, Rh, Ir, Os and mixtures thereof.

The hydrogenation catalyst preferably comprises palladium on carbon.

Step (iv) of the process according to the present invention results in a hydrogenated solution. This solution comprises FDCA and some hydrogenation products. The hydrogenation products suitably comprise no HMFA or only a minor amount of HMFA. Since HMFA is only present in a small amount, the FDCA in the hydrogenated solution can be recovered by crystallization in a satisfactory purity. The crystallization conditions are well known to the skilled person. The crystallization can easily be accomplished by allowing the hydrogenated solution to cool from the hydrogenation temperature to a temperature in the range of 0 to 80° C., whereby the FDCA in the hydrogenated solution will start to crystallize. Thereafter the crystallized FDCA is suitably separated from the polar solvent in the hydrogenated solution, e.g. by filtration. Since HMFA is better soluble in the polar solvent than FDCA the filtrate will contain HMFA and other hydrogenation products of FFCA, and the filtered FDCA has a high purity. If desired, the filtered FDCA may be further purified, e.g. by one or more re-crystallizations or by re-slurrying. The HMFA is suitably recycled to the oxidation process in step (i) of the process according to the present invention.

The steps (i) to (v) of the process according to the present invention can be carried out in a batch mode or in continuous mode. The process comprising steps (i) to (v) is preferably carried out as a continuous process. The process may be carried out in a number of reactors in series. The process may comprise a separate oxidation reactor, a separate hydrolysis reactor and a separate hydrogenation reactor. Between the reactors, other equipment for separation and/or other treatment techniques, such as washing or filtration or crystallization may be provided. The reactors may be selected from a variety of reactor types. Suitable reactors are continuous stirred tank reactors, bubble column reactors, trickle bed reactors and plug flow reactors. These reactors are particularly suitable when the process is carried out as a continuous process.

Since it was found that the presence of the hydrogenation catalyst also benefits the conversion of esters of FDCA it has become advantageous to carry out the steps (iii) and (iv) of the process of the present invention in a single reactor comprising a hydrolysis zone and a hydrogenation zone. In such a reactor, the ester-containing solution is first passed through a hydrolysis zone wherein the solution is kept for a sufficiently long time to achieve hydrolysis. The duration can be determined by the skilled person. Typically, the solution is kept for a period in the range of 1 min to 6 hours, preferably 1 to 5 hours to achieve hydrolysis. Before the solution is passed into the hydrolysis zone, the solution is contacted with hydrogen-containing gas so that hydrogen is dissolved into the solution. Subsequently, the solution containing the hydrolyzed FDCA and FFCA is then passed through a bed of catalyst for a time sufficient to hydrogenate the FFCA to the desired hydrogenation products.

The single reactor may be formed similar as the reactor according to U.S. Pat. No. 5,420,344. Such a reactor suitably comprises an inlet for hydrogen at the top of the reactor and an inlet for the acid composition solution in the upper part of the reactor. The solution may suitably contain the oxidation product of an alkoxymethylfurfural, such as MMF, optionally mixed with HMF. The oxidation product is suitably dissolved in water and optionally another solvent before being passed into the reactor to yield a solution comprising FDCA, FFCA and esters of FDCA and FFCA. The inlet for the solution debouches into an area where the solution is kept and is allowed to flow into the reactor space via an overflow wall. Hydrogen is supplied from the inlet at the top of the tower. Hydrogen will typically sufficiently dissolve in the acid composition solution at the prevailing temperature and pressure. However, additional hydrogen-containing gas may be supplied along the flow path of the acid composition solution that is flowing down after the overflow, so that ample hydrogen is dissolved in the solution.

The solution is then passed into a space of the reactor that represents the hydrolysis zone. The solution is retained therein for a time sufficient to achieve hydrolysis. The hydrolysis zone may be provided with a hydrolysis catalyst. However, as indicated above, the presence of such a catalyst is not required, as the acid in the solution itself may already provide catalytic activity. If a hydrolysis catalyst is contemplated, it is desirable to employ a solid hydrolysis catalyst. Suitable hydrolysis catalysts include acid zeolites and acid ion exchangers. These catalysts allow for an easy application of a plug flow mode. In this way the level of back-mixing is avoided and the hydrolysis reaction may proceed to equilibrium. The presence of a hydrolysis catalyst is however not required. If no hydrolysis catalyst is present it may be desirable to allow the solution to pass along internals and/or a packing to avoid back-mixing.

The solution is subsequently distributed over a bed of catalyst that is present in the body of the reactor, representing the hydrogenation zone. The distribution may be accomplished by any means, e.g. via a partition plate. The catalyst bed contains a bed of hydrogenation catalyst. The solution is passed through the catalyst bed together with hydrogen. Any remaining esters of FDCA, if present, are hydrolyzed and any FFCA or FFCA ester is hydrogenated in the catalyst bed. Finally, the hydrogenated solution is withdrawn from the reactor via an outlet at the bottom of the reactor.

The residence time of the solution in the hydrolysis zone can be adjusted such that the hydrolysis reaction between the esters of FDCA and FFCA reaches equilibrium. Since the conversion of ester of FDCA is further accelerated in the hydrogenation zone in the presence of the hydrogenation catalyst the residence time in the hydrolysis zone may be adjusted such that a minor amount of ester remains. Continuously, some of the hydrolyzed product, i.e. the crude acid composition solution, is passed to the hydrogenation zone. In operation, a bed of heterogeneous catalysts, such as a Group 8, 9 or 10 metal on carbon, will be provided in the hydrogenation zone. The crude acid composition solution is passed along the heterogeneous catalyst in the hydrogenation zone. Hydrogen that is necessary for the hydrogenation is supplied through via the dissolved hydrogen. Since the contact time of the crude acid composition solution with the hydrogenation catalyst and the hydrogen is relatively short, the hydrogenation zone may be relatively small, compared to the hydrolysis zone. Advantageously the amount of hydrogen that is supplied is adjusted such that the amount of hydrogen suffices to hydrogenate the FFCA in the crude acid composition solution so that only hardly any excess of hydrogen needs to be removed. This provides for the situation that the reactor does not require a gas outlet. If there is any excess hydrogen or if there is any diluent gas that is comprised in the hydrogen-containing gas such gas may be withdrawn from the reactor together with the hydrogenated product and be recovered, e.g. via a flash evaporation.

By combining the hydrolysis zone and the hydrogenation zone in a single reactor, the skilled person is enabled to conduct two steps in an efficient and economic way.

In step (v) the separation yields the purified acid composition comprising 2,5-furandicarboxylic acid. The separation is achieved by crystallization. The recovery of purified acid composition may further involve filtration or any other solids/liquid separation, washing and/or drying methods. The purified acid composition may also be re-crystallized.

As the present invention is particularly suitable for a process wherein a part of the oxidation product is subjected to a pre-hydrolysis step the present invention also provides a process for the preparation of a purified acid composition comprising 2,5-furandicarboxylic acid, comprising (a) oxidizing a feedstock containing 5-alkoxymethylfurfural to an oxidation product comprising FDCA, FFCA, and esters of FDCA and, optionally, esters of FFCA;

(b) separating the oxidation product into at least an oxidation product solids fraction comprising FDCA, and an oxidation product liquid fraction comprising ester of FDCA;

(c) pre-hydrolyzing at least a portion of the oxidation product liquid fraction to obtain a pre-hydrolyzed composition comprising FDCA and ester of FDCA;

(d) combining at least a portion of the oxidation product solids fraction with at least a portion of the pre-hydrolyzed composition, to obtain a combined part of the oxidation product;

(e) optionally, dissolving at least part of the combined part of the oxidation product in a polar solvent to obtain a solution of oxidation product, comprising FDCA, FFCA and esters of FDCA and optionally, FFCA;

(f) hydrolyzing the at least part of the combined part of the oxidation product in the presence of water, thereby hydrolyzing at least esters of FDCA and, optionally, of FFCA to obtain an aqueous solution of an acid composition;

(g) contacting at least part of the solution of the acid composition obtained in step (f) with hydrogen in the presence of a hydrogenation catalyst to hydrogenate FFCA to hydrogenation products, yielding a hydrogenated solution; and (h) separating at least a portion of the FDCA from at least part of the hydrogenated solution by crystallization. The product obtained in step (h) is the desired purified acid composition.

BRIEF DESCRIPTION OF THE DRAWINGS

The invention is illustrated by means of the figures, showing schematically flow diagrams and equipment for use in the present invention.

DETAILED DESCRIPTION OF THE INVENTION

Figure 1:
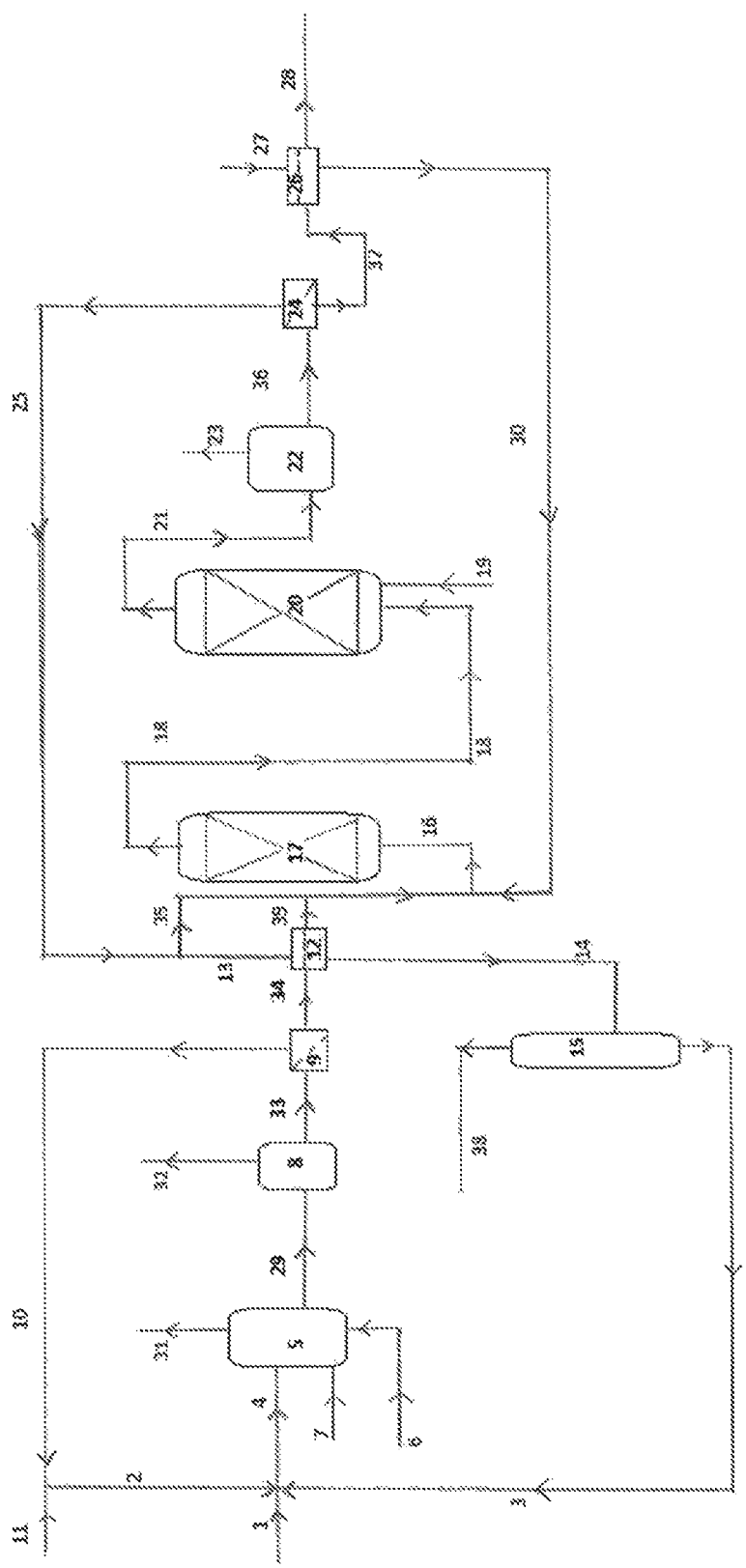
FIG. 1 shows a schematic process scheme of a suitable manner to carry out the process of hydrolysis and hydrogenation according to the present invention.

FIG. 1 shows a stream (1) containing primarily methoxymethyl furfural (MMF) that is combined with a recycled acetic acid rich stream (2) and a water rich stream (3) also containing recycled catalyst. The streams are combined into a stream (4) that is fed to an oxidation reactor (5). Oxygen-containing gas, such as air, is passed via a compressor (not shown) to the oxidation reactor (5) via a line (6). Make-up catalyst, typically comprising Co and Mn, and optionally Br, is fed into the oxidation reactor (5) via a line (7). It is understood that other oxidation catalysts may also be used. In the oxidation reactor MMF is oxidized to FDCA with the oxygen-containing gas in the presence of a catalyst that e.g. comprises Co, Mn, in acetic acid as solvent. FIG. 1 shows one reactor. The skilled person will realize that two or more reactors in series may also be used. Excess oxygen is discharged from the oxidation reactor (5) via a line 31. Oxidized product is withdrawn from the oxidation reactor via a line (29) and fed into a crystallization vessel (8). The crystallization may be conducted as an evaporative cooling crystallizer. Any acetic acid and/or water that are freed in the evaporative crystallization may be discharged from the crystallization vessel (8) via a line (32). A slurry of crude FDCA, that contains some FFCA, methyl ester of FDCA and catalyst, is fed via a line (33) to a filtration equipment (9), where the slurry is separated into an acetic acid-containing mother liquor stream (10) and a solid crude product that is passed via a line (34) to a washing unit (12). The acetic acid-containing mother liquor stream (10) is combined with a stream of make-up acetic acid, supplied via a line (11) to form the stream (2) that is combined with the MMF in stream (1) and water in stream (3). In some embodiments at least a part of the evaporated acetic acid and/or water in the line (8) is combined with the stream (10) (not shown). In such cases any water in stream (8) will typically be separated from the acetic acid, and the acetic acid will be combined with the compounds in the stream (10).

In the washing unit (12) the solid crude FDCA acid composition is washed with water that is supplied via a line (13). The water takes up acetic acid and the catalyst. The resulting liquid is discharged via a line (14) and fed to a distillation column (15). In the distillation column (15) some water is distilled off and removed overhead via a line (38). The bottom product of the distillation column (15) contains water, acetic acid and catalyst and is withdrawn as stream (3) that is combined with the MMF in stream (1) and acetic acid in stream (2). The figure shows the filtration and washing unit as two separate pieces of equipment. The skilled person will realize that the filtration and washing steps may be combined in one piece of equipment. In such a case the filtration will generate a filter cake, and the filter cake will be subjected to a washing treatment with water.

The solid crude FDCA acid composition obtained after washing is withdrawn via a line 39 and combined with some water from a line (35) and from another line (30) and as a combined stream (16) passed to a hydrolysis reactor (17). The residence time in the hydrolysis reactor (17) is selected such that the esters are hydrolyzed to methanol and FDCA. As indicated above, the hydrolysis reactor may be loaded with a bed of an acidic zeolite or ion exchange resin to catalyze the hydrolysis. The hydrolysis reactor may be operated at a temperature of about in the range of 120 to 200° C., e.g. 160° C. The hydrolysis product comprising FDCA, water and methanol, is withdrawn via a line (18) and fed to an hydrogenation reactor (20). The hydrogenation reactor (20) contains a bed of hydrogenation catalyst. Hydrogen that is fed into the hydrogenation reactor (20) via a line (19) reacts with FFCA to HMFA as main hydrogenation product, and the hydrogenation product, together with FDCA, water and some methanol, is removed from the reactor and via a line (21) fed into a second crystallizer (22).

As indicated above, it is also possible to combine hydrolysis reactor (17) and hydrogenation reactor (20) into one combined reactor. The combined stream (16) and hydrogen stream (19) may then be fed into the combined reactor in the upper part of this combined reactor. The stream (16) is maintained in a hydrolysis zone of the reactor and the combination of the thus hydrolyzed product and hydrogen is passed over a bed of hydrogenation catalyst, contained in the lower part of the combined reactor. The hydrogenation product is withdrawn at the bottom of the combined reactor. When the hydrogenation product contains any gas, such as excess hydrogen, such gas may be separated via a flash column (not shown). The remaining liquid stream, being the hydrogenation product that contains FDCA, water and methanol, is passed via the line 21 to the second crystallizer (22).

The crystallizer (22) is an evaporative cooling crystallizer wherein some water and methanol are liberated and withdrawn via a line (23). The water and methanol in line (23) may be separated and be re-used in the process. Methanol can for instance be recycled to the step wherein a carbohydrate with methanol is converted to MMF. Water that is separated from the mixture in line (23) can be used as wash water in one of the washing steps in the present process.

The solid FDCA that is obtained in the crystallizer (22) is passed as a slurry in a line (36) to a filtration equipment (24) where wet FDCA is separated from a mother liquor. The mother liquor contains water, optionally some methanol, HMFA, and optionally some other compounds that result from the hydrogenation of FFCA. The mother liquor is withdrawn from the filtration equipment (24) via a line (25). The line (25) is split into the line (35) to facilitate the transport of the crude solid FDCA acid composition from the washing unit (12) and into the line (13) that is used to wash the solid crude FDCA acid composition. If desired, a purge stream may be withdrawn from the line (25) (not shown). As indicated above, the washing liquid is withdrawn via the line (14). Any HMFA that is contained in the liquid in the line (13) will be withdrawn in the line (14), and via the distillation column (15) and the bottom product thereof in the line (3) will be recycled to the oxidation reactor. In this way no valuable product is lost.

The purified solid FDCA obtained in the filtration equipment (24) is passed through a line (37) to a washing unit (26) where it is washed with water, supplied via a line (27). The washing water is recovered via the line (30) and re-used. The washed purified FDCA acid composition is recovered from the washing unit (26) as the product stream (28).

As indicated above, the filtration equipment and washing unit can be combined into one piece of equipment. The skilled person will further realize that the crystallizer (22) can consist of one or more crystallizers. In such a case the second or subsequent crystallizer may be used to re-crystallize the product to obtain an even purer product.

Figure 2:
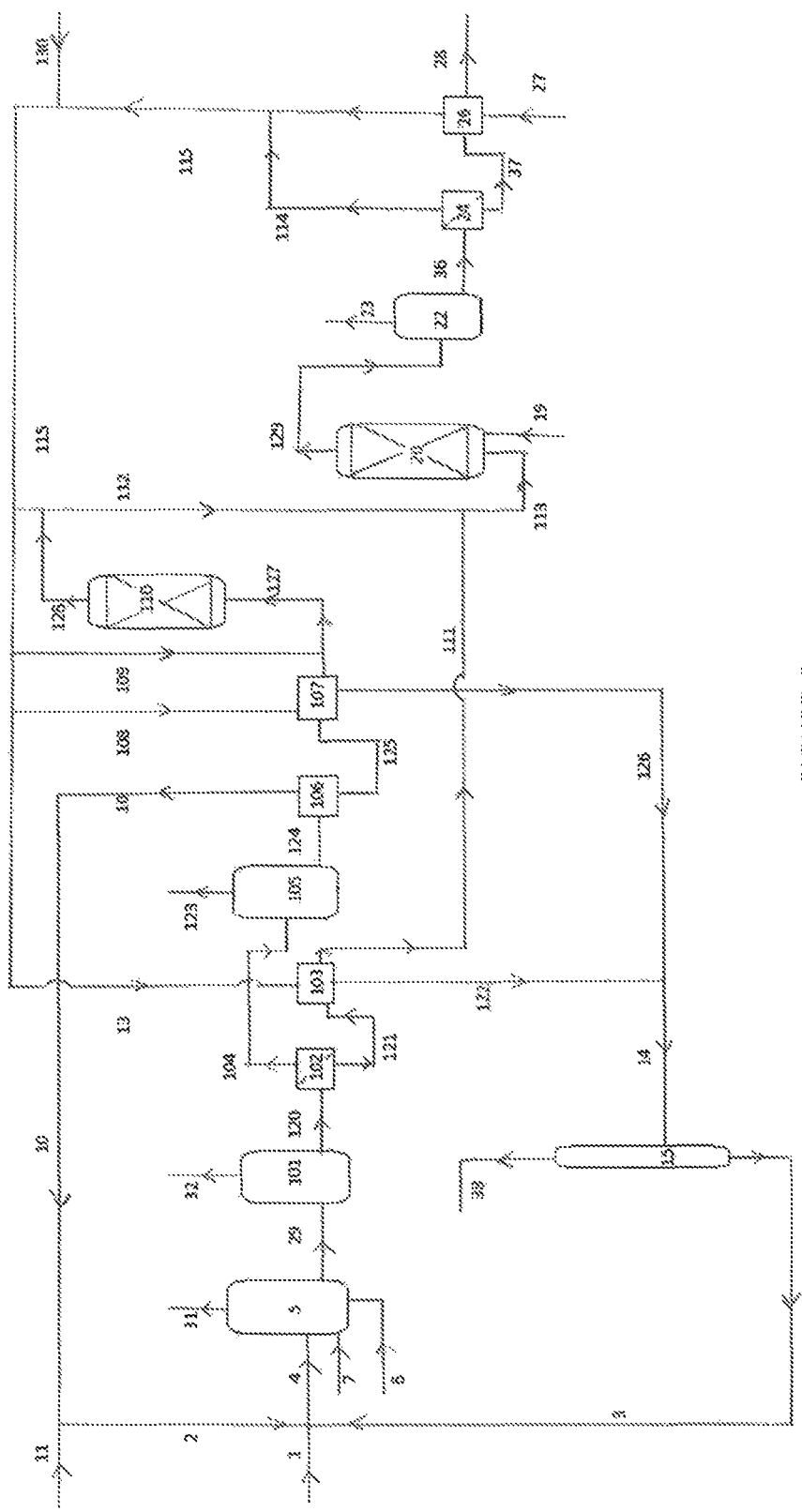
FIG. 2 shows another embodiment of such a process.

FIG. 2 shows a different embodiment of the process according to the invention. In FIG. 2 some streams have been given the same number as corresponding streams in FIG. 1.

MMF in stream (1) is combined with an acetic acid stream (2) and a water/catalyst stream (3) to a stream (4), which is passed to an oxidation reactor (5). In reactor (5) air that via a compressor through a line (6) is fed into the reactor (5), and catalyst, provided via a line (7), are combined with the MMF and allowed to react to yield a crude FDCA-containing acid composition. Excess oxygen is vented via a line (31). The crude FDCA-containing acid composition is passed via a line (29) to a first crystallizer (101). In crystallizer (101) only part of the crude acid composition is crystallized, yielding relatively pure FDCA. Crystallizer (101) is an evaporative cooling crystallizer, yielding a stream of acetic acid and water, discharged via a line (32), and a stream (120) comprising a slurry of the FDCA-containing acid composition and acetic acid. The FDCA-rich and acetic acid-rich slurry is passed to filtration equipment (102) via the line (120). In the filtration equipment (102), acetic acid-containing mother liquor (still containing a substantial amount of the methyl ester of FDCA and some FFCA) is separated from the crystallized FDCA and withdrawn via a line (104). The filtered solid FDCA is passed via a line (121) to a washing unit (103) where it is washed with water supplied via a line (13). The used wash water containing acetic acid and catalyst is withdrawn via a line (122). The washed FDCA is withdrawn via a line (111).

The acetic acid-containing mother liquor in the line (104) is passed to a second evaporative crystallizer (105). Further acetic acid and water is vented via a line (123). Via a line (124) a slurry of crystallized FDCA, containing FFCA and the methyl ester of FDCA, is fed into a filtration equipment (106) where the solid material is separated from a mother liquor. The mother liquor comprises acetic acid and is withdrawn via a line (10). The streams (32) and (123) may be combined with the stream (10), optionally after separation of at least part of the water contained in the streams (32) and (123). The combined stream (10) is supplemented with make-up acetic acid from a line (11) and the combined stream is passed as stream (2) to the MMF feedstock in stream (1) and to the oxidation reactor (5).

The crude FDCA-containing acid composition that is recovered as filter cake is passed via a line (125) to a washing unit (107) where it is washed with water, supplied via a line (108).

Alternatively, the evaporative crystallizer (105) is operated such that all liquid is evaporated via line (123) and a solid remains. Evidently, no filtration is needed and the solids are passed directly to the washing unit (107). The vaporized liquid that is withdrawn via the line (123) is then combined with the make-up acetic acid in line (11) and then passed further as line (2).

The wash water is recovered as stream (126). The stream (126) and (122) are combined to form a stream (14) which is passed to a distillation column (15) to separate water, discharged via a line (16), from the bottom product comprising water, acetic acid and oxidation catalyst, withdrawn via the line (3) that is combined with MMF and acetic acid, and recycled to the oxidation reactor.

The crude acid composition that is recovered in the washing unit (107) contains an amount of the monomethyl ester of FDCA, i.e. FDCA-ME. Therefore it is passed to a hydrolysis reactor (110) via a line (127). A stream comprising recycled water is fed into the line (127) through a line (109) to facilitate the transport of the acid composition. The hydrolysis reactor may be provided with a bed of heterogeneous catalyst to facilitate the hydrolysis. It is observed that the hydrolysis reactor can be smaller than in the process according to FIG. 1, as a smaller stream is passed through the hydrolysis reactor.

The hydrolysis product comprising FDCA, water, methanol and some FFCA and some FDCA-ME, is withdrawn from the hydrolysis reactor (110) through a line 128 and added to an aqueous stream in a line (112). The aqueous stream in the line (112) is combined with washed FDCA in the line (111) to form a stream (113), which is passed to a hydrogenation reactor (20). Hydrogen, supplied to the hydrogenation reactor (20) via a line (19), is reacted with FFCA supplied together with FDCA by the line (113), over a bed of a hydrogenation catalyst. The hydrogenated product, comprising HMFA, is passed via a line (129) to an evaporative cooling crystallizer (22), wherein some water and methanol are liberated and withdrawn via a line (23). The methanol and water may be re-used in the process as described above.

Figure 3:
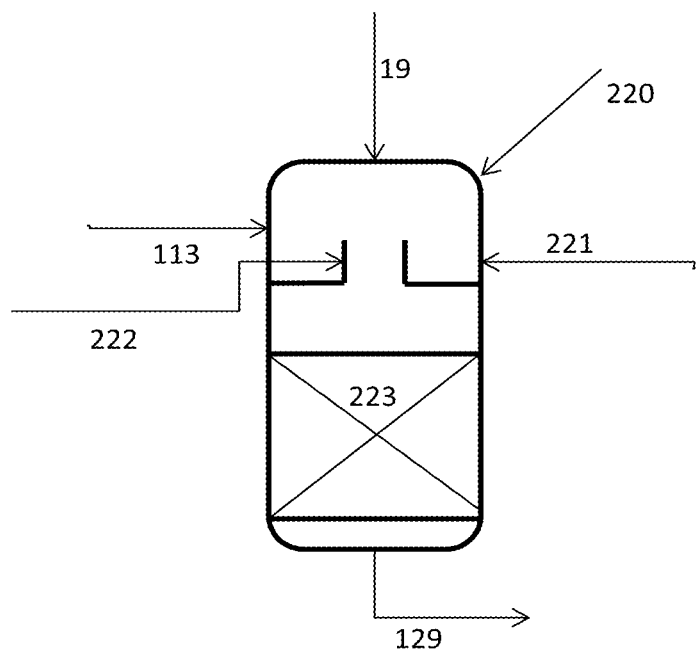
FIG. 3 shows a suitable reactor containing a hydrolysis zone and a hydrogenation zone.

Alternatively, in reactor (110) a pre-hydrolysis is carried out. A pre-hydrolyzate is then obtained in the line (128) before it is combined with the aqueous stream in the line (112). In such a case water in the aqueous stream of the line (112) is removed via evaporation or crystallization and filtration (not shown) to yield a solids pre-hydrolyzate solids fraction. The pre-hydrolyzate solids fraction may be combined with the washed FDCA from the line (111) and the combination may be dissolved. As also the combination of the solids fractions contains some FDCA-ME, the solution of the combined solids fractions is fed via the line (113) to a variation of the hydrolysis reactor (20) as shown in FIG. 3. This figure shows a reactor (220) into which hydrogen is fed via the line 19 and the solution of the combined solids fractions is fed into the reactor via the line (113). The solution from the line (113) is passed into a hydrolysis zone (221). This zone is formed by an annular area inside the reactor (220) which zone comprises an overflow wall (222). The solution is kept in the hydrolysis zone for a period to allow the hydrolysis reaction to take place. The excess solution will flow over the wall (222) and drop onto a bed of hydrogenation catalyst (223). The solution will be contacted with the hydrogenation catalyst and hydrogen, fed via the line (19). During the contact further hydrolysis may take place and the effluent, comprising mainly FDCA and solvent is withdrawn from the reactor (220) via a line (129). The effluent, further comprising HMFA, and optionally other compounds such as MFA, is treated as described above, i.e. it is passed via the line (129) to an evaporative cooling crystallizer (22), wherein some water and methanol are liberated and withdrawn via a line (23) (cf. FIG. 2). The methanol and water may be re-used in the process as described above. In processes wherein a pre-hydrolysis is carried out in addition to the hydrolysis in a reactor with a hydrolysis zone and a hydrogenation zone, the duration of the pre-hydrolysis is suitable from 1 to 5, preferably from 1 to 4 hours. The hydrolysis in the hydrolysis zone is then suitably from 1 to 60, suitably from 1 to 15 min.

As shown in FIG. 2, via a line (36) a slurry of crystallized purified FDCA is passed to filtration equipment (24) where wet purified FDCA is separated from a mother liquor that comprises water and HMFA. The mother liquor is withdrawn via a line (114). The wet purified FDCA is recovered through a line (37) and fed to a washing unit (26), where it is washed with water, supplied via a line (27). The wash water is withdrawn via a stream (115) to which the stream in the line (114) is added. The stream in the line (115) is split into the streams in the lines (112), (109), (108) and (13). Via the lines (115), (13), (122), (14), and (3) HMFA is recycled to the oxidation reactor (5) where it can be oxidized to FDCA. If needed, the amount of water in the line (115) can be supplemented by make-up water that can be supplied via a line (130).

Washed purified FDCA acid composition is recovered from the washing unit (26) as the product stream (28). Optionally, the purified acid composition can be further dried in a drying unit.

The process schemes of FIGS. 1 and 2 are schematic. Auxiliary equipment, such as pumps, heating or cooling means, compressors or expanders, valves and control means have not been shown in the Figures.

The invention will be further illustrated by means of the following examples.

EXAMPLES

The following experiments were conducted in a stainless steel reactor wherein a bed of solid catalyst was placed. The catalyst bed was kept at the same temperature. Feedstock containing FDCA and FFCA was fed over the bed of catalyst. The feedstock was an aqueous stream containing 0.5% wt of crude FDCA composition. The crude FDCA composition consisted of 98.0% wt of FDCA, 1.0% wt of FFCA, and about 1.0% wt of the monomethyl ester of FDCA (FDCA-ME). The composition further contained some ppm of the components of the oxidation catalyst, viz. cobalt, manganese and bromine.

Hydrogen-containing gas, consisting of 10% vol hydrogen and 90% vol nitrogen, was used for the hydrogenation.

The catalysts used were Catalyst 1, comprising 5% wt palladium on carbon and Catalyst 2, comprising 0.43% wt palladium on carbon.

The experiments were conducted as follows. The reactor was charged with a desired load of the desired catalyst. The bed of catalyst was vented several times with hydrogen to remove any oxygen. Unless otherwise indicated, the reactor was subsequently pressurized with the hydrogen-containing gas to a pressure of 15 bar (at 20° C.) and heated to the desired reaction temperature before the feedstock was passed over the bed of catalyst with the desired space velocity, expressed as weight hourly space velocity (WHSV) in grams of feedstock per gram of catalyst per hour. The Tables may also contain the contact time or residence time.

Example 1

In order to show the influence of the reaction temperature on the conversion of the FFCA to HMFA and MFA Catalysts 1 and 2 were used in experiments wherein the above feedstock was passed over beds of the two catalysts with different space velocities and at different reaction temperatures. From the reactor effluent the amounts of FFCA, HMFA and MFA were determined. The results are shown in Table 1. The amounts of FFCA, HMFA and MFA are expressed as mass %, based on the amount of FFCA in the feedstock.

TABLE 1

| Exp. No. | Catalyst | Contact time, min | Temp., ° C. | FFCA, mass % | HMFA, mass % | MFA, mass % |
|---|---|---|---|---|---|---|
| 1 | 1 | 0.15 | 160 | 0 | 72 | 17 |
| 2 | 2 | 0.15 | 160 | 4 | 85 | 6 |
| 3 | 1 | 3.0 | 160 | 0 | 0 | 10 |
| 4 | 2 | 3.0 | 160 | 0 | 0 | 20 |
| 5 | 1 | 0.12 | 170 | 0 | 75 | 18 |
| 6 | 2 | 0.15 | 170 | 10 | 70 | 7 |
| 7 | 1 | 3.0 | 170 | 0 | 0 | 9 |
| 8 | 2 | 3.0 | 170 | 0 | 5 | 10 |
| 9 | 1 | 0.12 | 180 | 0 | 62 | 20 |
| 10 | 1 | 3.0 | 180 | 0 | 0 | 8 |
| 11 | 2 | 3.0 | 180 | 0 | 0 | 5 |
| 12 | 1 | 0.12 | 190 | 15 | 58 | 12 |
| 13 | 1 | 0.23 | 190 | 0 | 50 | 25 |
| 14 | 1 | 1.0 | 190 | 0 | 0 | 15 |
| 15 | 2 | 1.0 | 190 | 0 | 0 | 5 |

Example 2

To show the catalytic effect of the hydrogenation catalyst on the hydrolysis reaction Catalysts 1 and 2 were tested at different hydrogenation conditions as to space velocity and temperature. In addition, blank experiments were conducted at the same conditions, but in the presence of inert ceramic particles instead of catalyst particles. The feedstock was similar to that described in Example 1. The amount of FDCA-ME was measured for the each of the effluents, and expressed as weight percent of the total liquid effluent. The results are shown in Table 2.

TABLE 2

| Experiment No. | Catalyst | WHSV, hr$^{-1}$ | Contact time, min | Temperature, ° C. | FDCA-ME, % wt |
|---|---|---|---|---|---|
| 16 | Blank | — | — | 160 | 0.75 |
| 17 | 1 | 267 | 0.22 | 160 | 0.60 |
| 18 | 2 | 267 | 0.22 | 160 | 0.65 |
| 19 | Blank | — | — | 160 | 0.75 |
| 20 | 1 | 160 | 0.37 | 160 | 0.60 |
| 21 | 2 | 160 | 0.37 | 160 | 0.60 |
| 22 | Blank | — | — | 160 | 0.75 |
| 23 | 1 | 40 | 1.5 | 160 | 0.40 |
| 24 | 2 | 40 | 1.5 | 160 | 0.18 |
| 25 | Blank | — | — | 160 | 0.75 |
| 26 | 1 | 20 | 3.0 | 160 | 0.25 |
| 27 | 2 | 20 | 3.0 | 160 | 0.0 |
| 28 | Blank | — | — | 190 | 1.10 |
| 29 | 1 | 267 | 0.22 | 190 | 0.90 |
| 30 | 2 | 267 | 0.22 | 190 | 0.90 |
| 31 | Blank | — | — | 190 | 1.10 |
| 32 | 1 | 160 | 0.37 | 190 | 0.80 |
| 33 | 2 | 160 | 0.37 | 190 | 0.82 |
| 34 | Blank | — | — | 190 | 1.10 |
| 35 | 1 | 40 | 1.5 | 190 | 0.30 |
| 36 | 2 | 40 | 1.5 | 190 | 0.17 |
| 37 | Blank | — | — | 190 | 1.10 |
| 38 | 1 | 20 | 3.0 | 190 | 0.17 |
| 39 | 2 | 20 | 3.0 | 190 | 0.0 |

Example 3

To show the difficulties of separating FDCA from the hydrogenation products of FFCA the following experiments were conducted.

Pure FDCA was mixed with a pure contaminant in an amount of up to 2% wt, based on the amount of FDCA. The mixture was dissolved in water to a concentration of about 4% wt of FDCA by heating. FDCA was crystallized by cooling the solution under controlled cooling rates. The FDCA crystals were filtered at 80, 50 and 20° C. and the levels of each contaminant in the wet crystals were determined. The results are shown in Table 3 below. The levels are shown as percentages of the amounts of the contaminants that were added to the pure FDCA.

The results show that many compounds that may be produced in the hydrogenation of FFCA are difficult to separate from FDCA. The best separation can be obtained with HMFA.

TABLE 3

| Contaminant | % @ 20° C. | % @ 50° C. | % @ 80° C. |
|---|---|---|---|
| 5-hydroxymethyl furan-2-carboxylic acid (HMFA) | 8 | 4 | 4 |
| furan-2-carboxylic acid (FCA) | 45 | 45 | 44 |
| 5-methyl-furan-2-carboxylic acid (MFA) | 22 | 17 | 14 |
| 5-formyl-furan-2-carboxylic acid (FFCA) | 65 | 58 | 54 |
| monomethyl ester of 2,5-furandicarboxylic acid (FDCA-ME) | 88 | 87 | 85 |

Example 4

To show the efficacy of the present process on more concentrated solutions of FDCA, FDCA solutions of up to 30% wt, based on the total solution, were tested. The solutions were prepared by dissolving 10, 20 or 30% wt of crude FDCA in water. The crude FDCA (cFDCA) contained 98.0% wt of FDCA, 1.0% wt of FFCA, and about 0.9% wt of the monomethyl ester of FDCA (FDCA-ME) and 0.1% wt of FCA (furan carboxylic acid). The solutions were contacted with a slurry of catalyst, comprising 0.43% wt palladium on carbon at different temperatures and at different space velocities. The space velocities were expressed as weight hourly space velocity (as gr cFDCA/gr catalyst/hour). The hydrogenated solutions were analyzed for the presence of hydrogenation products. For the hydrogenated solutions the percentage of FDCA recovered was determined.

In Tables 4 to 6 the results of the hydrogenation experiments are shown at 160° C., at 180° C., and 190° C., whilst the pressure at room temperature of the hydrogen-containing gas (10 vol % $H_2$/90 vol % $N_2$) was 5 bar, 10 bar and 15 bar, respectively. The amounts of FFCA, HMFA and MFA are shown as analyzed from the hydrogenated solutions. In addition, the amounts of FCA, which may be formed as the result of the decarboxylation of the starting material, as well as the amounts of FDCA-ME, have been determined. The amounts of FDCA shown have been calculated as the percentage of the amount of FDCA that was passed to the catalyst bed.

TABLE 4

Hydrogenation of 10% wt crude FDCA solution at 160° C./5 bar pressure

| Exp. No. | WHSV, $h^{-1}$ | FFCA, ppmw | HMFA, ppmw | MFA, ppmw | FCA, % wt | FDCA-ME, % wt | FDCA, % wt |
|---|---|---|---|---|---|---|---|
| 40 | 5 | 0 | 294 | 93 | 0.1 | 0.8 | 99 |
| 41 | 10 | 0 | 445 | 98 | 0.1 | 0.9 | 99 |
| 42 | 95 | 221 | 667 | 16 | 0.1 | 0.9 | 99 |

TABLE 5

Hydrogenation of 20% wt crude FDCA solution at 180° C./10 bar pressure

| Exp. No. | WHSV, $h^{-1}$ | FFCA, ppmw | HMFA, ppmw | MFA, ppmw | FCA, % wt | FDCA-ME, % wt | FDCA, % wt |
|---|---|---|---|---|---|---|---|
| 43 | 10 | 0 | 0 | 11 | 0.5 | 0.4 | 99 |
| 44 | 20 | 0 | 0 | 0 | 0.4 | 0.4 | 99 |
| 45 | 44 | 0 | 24 | 0 | 0.4 | 0.4 | 99 |
| 46 | 92 | 160 | 49 | 0 | 0.4 | 0.4 | 99 |

TABLE 6

Hydrogenation of 30% wt crude FDCA solution at 190° C./15 bar pressure

| Exp. No. | WHSV, $h^{-1}$ | FFCA, ppmw | HMFA, ppmw | MFA, ppmw | FCA, % wt | FDCA-ME, % wt | FDCA, % wt |
|---|---|---|---|---|---|---|---|
| 47 | 15 | 0 | 0 | 0 | 0.6 | 0.4 | 99 |
| 48 | 30 | 0 | 0 | 0 | 0.6 | 0.4 | 99 |
| 49 | 56 | 0 | 0 | 0 | 0.7 | 0.4 | 99 |
| 50 | 125 | 193 | 0 | 0 | 0.5 | 0.4 | 99 |

The above results show that the formation of undesired MFA by-product can substantially be avoided by subjecting the crude FDCA compositions to hydrogenation at various temperatures and at high WHSV values.

Example 5

To show the influence of the presence of FDCA-ME on the purity of the crystallized purified FDCA, and in particular on the level of FCA in the crystallized FDCA, aqueous solutions were prepared from FDCA compositions which comprised 1% wt FCA, various amounts of FDCA-ME and the balance being FDCA. The concentration of the FDCA compositions in water was 0.04 g/ml. The solutions were subjected to FDCA crystallization by cooling from 140 to 25° C. The solids obtained were filtered to obtain a wet cake and the wet cake was analyzed. Similarly, solutions were prepared from FDCA compositions wherein the amount of FDCA-ME was kept constant at 0.5% wt and the amounts of FCA were varied. In the Table 7, the compositions of the FDCA compositions in the starting solutions are given, and the relative amounts of FCA in the wet cakes are shown, all based on the amounts of FCA, FDCA-ME and FDCA.

TABLE 7

| FDCA comp. # | Composition of starting FDCA composition, % | | | FCA in wet cake, % |
|---|---|---|---|---|
| | FDCA-ME | FCA | FDCA | |
| 1 | 1.3 | 1.0 | Balance | 0.8 |
| 2 | 0.7 | 1.0 | Balance | 0.4 |

TABLE 7-continued

| FDCA comp. # | Composition of starting FDCA composition, % | | | FCA in wet cake, % |
|---|---|---|---|---|
| | FDCA-ME | FCA | FDCA | |
| 3 | 0.5 | 1.0 | Balance | 0.4 |
| 4 | 0.14 | 1.0 | Balance | 0.2 |
| 5 | 0.07 | 1.0 | Balance | 0.2 |
| 6 | 0.5 | 1.05 | Balance | 0.4 |
| 7 | 0.5 | 0.3 | Balance | 0.3 |
| 8 | 0.5 | 0.1 | Balance | 0.1 |
| 9 | 0.5 | 0.04 | Balance | 0.04 |

From the results it is apparent that the amount of FDCA-ME influences the relative amounts of FCA in the wet cake, i.e. the purified crystallized FDCA composition. This highlights the desirability to hydrolyze the FDCA-ME present in the oxidation product as completely as feasible.

The invention claimed is:

1. A process for the preparation of a purified acid composition comprising 2,5-furandicarboxylic acid, comprising:
   (i) oxidizing a feedstock containing 5-alkoxymethylfurfural to an oxidation product comprising 2,5-furandicarboxylic acid (FDCA) and 2-formyl-furan-5-carboxylic acid (FFCA), and esters of FDCA and, optionally, esters of FFCA;
   (ii) optionally, dissolving the oxidation product in a polar solvent to obtain a solution of the oxidation product, comprising FDCA, FFCA and esters of FDCA and, optionally, esters of FFCA;
   (iii) hydrolyzing the oxidation product in the presence of water, thereby hydrolyzing part or all of the esters of FDCA and, optionally, the esters of FFCA to obtain an aqueous solution of an acid composition comprising FDCA, FFCA and ester of FDCA in an amount below the amount of ester of FDCA in the solution of the oxidation product;
   (iv) contacting the solution of the acid composition obtained in step (iii) with hydrogen in the presence of a hydrogenation catalyst to hydrogenate FFCA to hydrogenation products, yielding a hydrogenated solution; and
   (v) separating the FDCA from part or all of the hydrogenated solution by crystallization;
   wherein the acid composition solution is contacted with hydrogen at a temperature in the range of 150 to 200° C. and a contact time with the hydrogenation catalyst of at most 10 min.

2. The process according to claim 1, wherein the amount of ester of FDCA in the oxidation product that is hydrolyzed, comprises from 0.5 to 60 % wt of ester of FDCA, based on the amounts of FDCA, FFCA and esters of FDCA and FFCA.

3. The process according to claim 1, wherein the hydrolysis is carried out at conditions to obtain an aqueous solution of an acid composition with an amount of ester of FDCA of at most 1.0% wt, based on the amount of FDCA, FFCA, and esters of FDCA and FFCA.

4. The process according to claim 1, wherein in step (ii) the oxidation product is hydrolyzed by contacting the part or all of the oxidation product with water for a period from 1 to 360 minutes.

5. The process according to claim 1, wherein in step (ii) the oxidation product is hydrolyzed by contacting the part or all of the oxidation product with water at a temperature of 120 to 200° C. and a pressure of 5 to 80 bar.

6. The process according to claim 1, wherein in step (ii) the oxidation product is hydrolyzed by contacting the part or all of the oxidation product with water in the presence of a hydrolysis catalyst.

7. The process according to claim 1, wherein in step (ii) the oxidation product is hydrolyzed by contacting the oxidation product with water in the absence of a hydrolysis catalyst.

8. The process according to claim 1, wherein the oxidation product that is hydrolyzed has been obtained by:
   separating the oxidation product into an oxidation product solids fraction comprising FDCA, and an oxidation product liquid fraction comprising ester of FDCA;
   pre-hydrolyzing the oxidation product liquid fraction by contacting the oxidation product liquid fraction with water to obtain a pre-hydrolyzed composition comprising FDCA and ester of FDCA; and
   combining the oxidation product solids fraction with the pre-hydrolyzed composition.

9. The process according to claim 8, wherein a pre-hydrolyzate solids fraction is separated from the pre-hydrolyzed composition and the pre-hydrolyzate solids fraction is combined with the portion or all of oxidation product solids fraction.

10. The process according to claim 1, wherein in step (iv) FFCA is hydrogenated such that the hydrogenation products contain up to a minor amount of 2-methyl-furan-5-carboxylic acid (MFA).

11. The process according to claim 1, wherein in step (i) the feedstock is oxidized by means of an oxygen-containing gas in the presence of a catalyst comprising cobalt and manganese.

12. The process according to claim 11, wherein the catalyst comprises cobalt and manganese, and further comprises bromine.

13. The process according to claim 1, wherein the feedstock is oxidized at a temperature of from 60 to 220° C., at a pressure of from 5 to 100 bar and at a residence time of from 0.1 to 48 hours.

14. The process according to claim 1, wherein in step (iv) the pressure is in the range of 1 to 80 bar.

15. The process according to claim 1, wherein the polar solvent is selected from the group consisting of water, alcohols, acids and mixtures thereof.

16. The process according to claim 1, which is conducted as a continuous process.

17. The process according to claim 1, wherein steps (iii) and (iv) are carried out in a single reactor, comprising a hydrolysis zone and a hydrogenation zone.

18. A process for the preparation of a purified acid composition comprising 2,5-furandicarboxylic acid, comprising:
   (a) oxidizing a feedstock containing 5-alkoxymethylfurfural to an oxidation product comprising FDCA, FFCA, and esters of FDCA and, optionally, esters of FFCA;
   (b) separating the oxidation product into an oxidation product solids fraction comprising FDCA, and an oxidation product liquid fraction comprising ester of FDCA;
   (c) pre-hydrolyzing the oxidation product liquid fraction to obtain a pre-hydrolyzed composition comprising FDCA and ester of FDCA;
   (d) combining the oxidation product solids fraction with the pre-hydrolyzed composition, to obtain a combined part of the oxidation product;

(e) optionally, dissolving the combined part of the oxidation product in a polar solvent to obtain a solution of oxidation product, comprising FDCA, FFCA and esters of FDCA and optionally, FFCA;
(f) hydrolyzing the combined part of the oxidation product in the presence of water, thereby hydrolyzing the esters of FDCA and, optionally, of FFCA to obtain an aqueous solution of an acid composition;
(g) contacting a solution of the acid composition obtained in step (f) with hydrogen in the presence of a hydrogenation catalyst to hydrogenate FFCA to hydrogenation products, yielding a hydrogenated solution; and
(h) separating the FDCA from the hydrogenated solution by crystallization.

19. The process according to claim 18, wherein the acid composition solution is contacted with hydrogen at a temperature in the range of 150 to 200 ° C. and a contact time with the hydrogenation catalyst of at most 10 min.

* * * * *